United States Patent [19]

Ehrlich et al.

[11] 4,355,023

[45] Oct. 19, 1982

[54] ANTIBODY FRAGMENT COMPOSITIONS AND PROCESS

[75] Inventors: Paul H. Ehrlich, White Plains, N.Y.; Gary R. Matsueda, Winchester, Mass.; Michael N. Margolies; Edgar Haber, both of Weston, Mass.

[73] Assignee: The Massachusetts General Hospital, Boston, Mass.

[21] Appl. No.: 192,696

[22] Filed: Sep. 30, 1980

[51] Int. Cl.³ .......................................... A61K 39/395
[52] U.S. Cl. ................................ 424/85; 260/112 B; 424/101
[58] Field of Search .................... 260/112 B, 112.5 R; 424/85, 101; 435/68–71

[56] References Cited

PUBLICATIONS

Rosemblatt et al., Biochemistry, vol. 17, pp. 3877–3882, 1978.
Chemical Abstracts, vol. 91, p. 455, Abstract No. 106394a, 1979.

Primary Examiner—Blondel Hazel

[57] ABSTRACT

Immunologically active rabbit IgG antibody fragment compositions are produced by isolating the anti-light variable chain of rabbit IgG and/or the anti-heavy variable chain of rabbit IgG and combining them with each other or with the complementary heavy or light chain of rabbit IgG.

9 Claims, 8 Drawing Figures

ANTIBODY FRAGMENT COMPOSITIONS AND PROCESS

The invention described herein was made in the course of work under a grant or award from the Department of Health and Human Services.

BACKGROUND OF THE INVENTION

This invention relates to a process for making novel antibody fragment compositions and to the compositions so-produced.

Immunoglobulin polypeptide chains are composed of linear repeating regions of homologous sequence of about 110-120 amino acid residues in length. In a portion of the chains, the sequence of the amino acids is variable and the sequence variability is located in the amino-terminal one quarter of the heavy chain and the amino-terminal one half of the light chain. Presently, it is believed that these variable regions constitute the antibody-combining sites and their participation in antigen binding has been confirmed directly by x-ray crystallography. Furthermore, x-ray studies have supported the hypothesis that each homology region is an independent domain that has a tightly folded structure stabilized by a disulfide bond. This domain theory has been verified further by the isolation of a fully active hapten-binding fragment consisting of only the variable region of the heavy chain ($V_H$) and the variable region of the light chain ($V_L$) from DNP-binding murine myelomas MOPC 315 and XRPC-25 (Hochman et al, Biochemistry, Vol. 15, p. 2706 (1976) and Sharon et al, Biochemistry, Vol. 15, p. 1591 (1976)).

Immunoglobulin fragments comprising variable domains have been isolated from heterogeneous IgG and myeloma proteins for which no corresponding hapten or antigen is known. It would be desirable to provide both the $V_H$ and $V_L$ fragments from homogenous IgG so that compositions could be produced therefrom that bind specific antigens. Presently, two methods employing enzymatic cleavage have been reported for the production of rabbit antibody $V_H$, i.e., Mole et al., J. Immunol., Vol. 114, p. 1442 (1975) and Rosemblatt et al., Biochemistry, Vol. 17, p. 3877 (1978). The $V_H$ from a homogenous antibody also showed a partial regaining of binding activity upon recombination with the light chain, Rosemblatt et al., supra. Prior to the present invention, no method has been available for producing an active $V_L$ chain which can be utilized to form compositions having specific antigen binding activity. This is because rabbit IgG and κ chains contain, in addition to the intradomain disulfide bonds, an extra disulfide bridge spanning the variable and constant domains. Thus, these two regions in the acid cleaved light chain remain associated. In order to isolate the $V_L$ from $C_L$, the interdomain disulfide bridge must be reduced and the domain then separated.

It would be highly desirable to provide a method for producing both the heavy variable fragment and the light variable fragment from homogenous rabbit IgG in order to permit production of antibody composition having a high affinity for specific antigen. Such compositions being of lower molecular weight than the normally produced rabbit IgG would be less immunogenic and more rapidly distributed in the blood and more rapidly excreted than the normally produced homogenous rabbit IgG antibody. Furthermore, it would be desirable to provide such variable fragments which are capable of regaining substantially all of their binding activity upon being recombined with either the complementary light chain or the complementary heavy chain.

SUMMARY OF THE INVENTION

The present invention provides methods for isolating both the heavy variable fragment and the light variable fragment from homologous rabbit IgG. The present invention also provides novel compositions prepared from the light variable fragment and/or the heavy variable fragment which compositions exhibit high activity against specific antigens. Unlike the heavy variable fragments obtained by prior art methods, the heavy variable fragment obtained by the process of this invention is capable of producing compositions which regain substantially all of the activity of the original IgG from which the heavy variable fragment was produced initially. The heavy variable fragment and the light variable fragment produced by this invention are combined with either the complementary heavy chain or light chain or the original IgG or are combined with each other to produce compositions having substantial activity against specific antigens and which are more rapidly distributed and excreted within and from the patient and which are far less immunogenic than the initial antibody from which they are produced.

DESCRIPTION OF SPECIFIC EMBODIMENTS

In accordance with this invention, the light chains and the heavy chains of homologous rabbit IgG antibody are treated separately in order to isolate the light variable fragment and the heavy variable fragment. Purification of the light variable fragment is based primarily on the use of an affinity chromatography technique wherein an antibody for the reduced and alkylated light constant fragment of the antibody ($C_L$) is bound to a chromatographic column so that a mixture of the light variable fragment ($V_L$) and the light constant fragment become separated by virtue of the affinity for the constant variable fragment by the complementary antibody bound to the chromatographic column while light variable fragment is allowed to pass through the column. In accordance with this invention, homogeneous rabbit IgG antibody is obtained from rabbit serum and purified such as by affinity chromatography, ion exchange chromatography or the like. The antibody is reduced and alkylated and the heavy and light chains are separated from each other such as by molecular exclusion chromatography. The separated light chains then are subjected to acid cleavage under mild conditions in order to maximize the yield of cleavage between aspartic acid at position 109 and proline at position 110.

The light constant chain antibody is prepared by first isolating the light constant chain of the rabbit IgG. The light constant chain is obtained by citra conylation of the epsilon-amino groups of the lysyl-residue contained in the light chain of the rabbit IgG. This reaction is carried out at a temperature between about 20° C. and 30° C. for a time of at least about 60 minutes with citraconic anhydride, maleic anhydride or mixtures thereof or the like. Thereafter, the light chains are subjected to tryptic digestion in order to cleave the peptide bonds carboxy-terminal to each arginyl-residue. The tryptic peptides from the reduced and alkylated light chains then are fractionated such as by gel filtration in order to recover the largest peptide which comprises the light chains constant domain. Generally, this largest peptide comprises the 62–211 residue. This peptide then is acid cleaved at a pH of between about 1.5 and about 2.5 in the presence of guanidinehydrochloride for at least about 50 hours, preferably between about 70 and about 80 hours. The acid cleaved reaction mixture then is subjected to column chromatography to recover the major light constant chain peptide which includes the 110–211 residue. This residue then is freed from salt by dialysis. It is preferred to conduct the acid cleavage under conditions to remove simultaneously the citraconyl or maleyl-groups from the peptides, namely, between about 1.5 and about 2.5 pH. The light constant chain then is insolubilized such as by reaction thereof with a cyanogen bromide-activated Sepharose, Sephadex, Agarose or the like. Generally, attachment of the light constant chain is effected to a pH of between about 6.5 and about 7.5 when the chain is dissolved in a suitable medium such as guanidine hydrochloride, urea or lithium bromide.

Antibodies specific for rabbit light chain constant reagent then are prepared by reducing disulfide bonds in nonchaotropic buffers and alkylating the light chains from pooled nonimmune rabbit Ig such as with iodoacetic acid or iodoacetamide. Thereafter, the reduced and alkylated light chains are acid cleaved such as under the acid conditions described above. The acid cleaved mixture then is applied to an equilibrated chromatographic column in order to separate cleaved from uncleaved chains. The fractions containing cleaved variable light chains and cleaved constant light chains then are pooled and freed from salt and may be lyophilized and stored for subsequent use or can be used immediately by suspending the light chains in a suitable buffer such as sodium phosphate, sodium acetate or potassium phosphate at a pH of between about 4 and 6, preferably at a pH of about 5. The light chains then are cross-linked such as with an aldehyde such as glutaraldehyde or formalin. The cross-linked light chains are purified such as by dialysis and then are administered (injected) to an animal species other than a rabbit such as sheep, mouse, guinea pig or goat in any manner well known in the art such as by immunizing the animal over a period of time sufficient to permit the animal to raise the complementary antibody. This is determined by periodically collecting antisera and testing the antisera for antibody such as by the conventional ring test using the fully reduced and alkylated nonimmune light chain as the antigen.

Upon determination that the animal, e.g. sheep antigen contains antibodies that react with the completely reduced and alkylated light chains, the antiserum is applied to the column containing the light constant chains linked to the Sepharose or Sephadex substrate. The antibody within the antiserum becomes linked to the immobilized light constant chain. Thereafter, the column is washed with eluant such as guanidine hydrochloride in order to dissociate the specific anti-light constant chain from the immobilized light constant chain antigen. The recovered eluant rich in the antibody then is dialyzed and concentrated such as by pervaporation. Thereafter, the recovered antibody is immobilized on a Sepharose or Agarose column in the manner described above for the corresponding antigen to form a specific anti-constant light chain immunoadsorbent.

The light variable chains are purified by affinity chromatography as follows: Specific acid cleaved light chains obtained by the procedure set forth above are reduced in a buffer and reacted with an excess of p-chloromercuribenzoate (PCMB). The resultant solution is purified such as by dialysis and clarified by centrifugation. The diluted solution then is applied to the chromatographic column having bound thereto the anti-light constant chain immunoadsorbent. Prior to applying the acid cleaved light chains, the column is equilibrated in a buffer such as phosphate buffered saline in a conventional manner. The anti-light constant chains are selectively removed from the acid cleaved light chain solution thereby selectively retaining the anti-light variable chains in solution which are passed through the column and recovered therefrom.

The anti-light variable chains obtained by the process of this invention alone do not exhibit antibody activity and must be combined either with the complementary heavy chain or with the complementary heavy variable chain fraction in order to reestablish antibody activity. Therefore, it is necessary to reoxidize the light variable chain in a manner which does not degrade the light variable chain peptide. The light variable chain recovered from the column first is purified such as by dialysis and then is reduced in a non-oxidizing atmosphere such as with dithiothreitol, 2-mercaptoethanol or the like such as in an inert atmosphere or in nitrogen. The reducing solution contains guanidine hydrochloride and Trishydrochloride at a pH of between about 8.0 and about 9.0 so that complete removal of $p$-mercuribenzoate groups which are attached to the cysteinyl residues. Alternatively, urea could be utilized rather than guanidine hydrochloride. In order to reestablish the intradomain disulfide bridge, the protein concentration is lowered to about 20, preferably less than about 30 $\mu$g/mL by dilution with buffer. Since the isolated light variable chain domain contains 3 cysteine residues, alkylation of the cysteine remaining after reformation of a single bridge is performed by incubation with iodoacetic acid or iodoacetamide. Thereafter, the light chain variable region domain can be purified such as by dialysis and stored in a protecting medium such as sodium acetate with sodium azide.

Combination of the anti-light variable chains with the complementary heavy chains or with the complementary variable heavy chains is accomplished by mixing said chains before or after removal of the chaotropic agents used to dissociate the chains.

The isolation of heavy variable chains from the rabbit IgG is based upon the use of cathepsin B which cleaves the IgG at a specific site in the molecule. The heavy chains are isolated following partial reduction of disulfide bonds followed by aminoethylation of the resulting cysteinyl residues to give 5-aminoethyl-cysteinyl residues. During reduction, a temperature of between about 25° C. and about 40° C., preferably about 37° C. is maintained. Aminoethylation can be conducted either subsequent to reduction or concomitantly therewith wherein the aminoethylating agent is added to the IgG together with the reducing agent such as dithiothreitol at a temperature of between about −5° C. and about 5° C., preferably at about 0° C. The product obtained then is purified such as by dialysis and chromatography. The purified aminoethylated heavy chain then is contacted with activated cathepsin B in order to cleave the heavy chain at the two adjacent cysteinyl residues at positions 133 and 134 on the peptide chain. The cathepsin B can be activated in any conventional manner such as with disodium ethylenediamine tetraacetic acid, dithiotheital, 2-mercatoethanal or the like and/or by heating to a temperature between about 25° C. and about 37° C. Generally, the ratio of the enzyme to the substrate is between about 5% and about 15% by weight, preferably between about 9% and about 11% by weight. Under these conditions, substantially complete digestion occurs generally within about 4 hours. The digestion product then is purified by passing the digestion product through a gel column. The heavy variable chain fragment then is isolated such as by the procedure set forth and then is applied to a reactive gel column in order to effect a binding thereof.

The heavy variable chain fragment by itself does not exhibit the desired antibody activity. In order to reactivate the heavy variable chain, it is combined either with the light variable chain fragment or with the light chain of the antibody by mixing the above composition in solution either before or after the removal of the chaotropic agents (guanidine or urea) in any manner well known in the art.

The following examples illustrate the present invention and are not intended to limit the same.

EXAMPLE I

This example illustrates the method of this invention for isolating homogenous rabbit antibody variable light chains.

The following abbreviations are used herein: Fv, Ig fragment composed of the variable region of light chain and the variable region of heavy chain; $V_H$, variable region of Ig heavy chain; $V_L$, variable region of Ig light chain; DNP, 2,4-dinitrophenyl; $C_L$, constant region of light chain; Pth, phenylthiohydentoin; NaDodSO$_4$, sodium dodecyl sulfate; DTT, dithiothreitol; PCMA, p-chloromercuribenzoate; GAB buffer, guanidine-acetate buffer [5 M guanidine hydrochloride (Gdn-HCl) and 0.1 M sodium acetate, pH 5.5]; PBS, phosphate-buffered saline (0.005 M potassium phosphate, 0.15 M NaCl, and 0.02% NaN$_3$, pH 7.0); S3, type III pneumococcal polysaccharide.

Protein concentrations were determined by amino acid analysis following 24 hours of hydrolysis at 110° C. in constant-boiling HCl in sealed evacuated tubes. Analyses were performed on a Durrum D-500 amino acid analyzer.

Automated Edman degradation was performed in a modified Beckman 890B sequencer using a 0.1 M Quadrol program described by Brauer et al., Biochemistry, Vol. 14, p. 3029 (1975). Phenylthiohydantoin (Pth) amino acids were identified and quantified by gas-liquid chromatography and high-pressure liquid chromatography, Margolies et al, Fed. Proc. Fed. Am. Soc. Exp. Biol., Vol. 38, p. 809 (1978). Thin-layer chromatography on polyamide sheets was also used, Summers et al., Anal. Biochem., Vol. 53, p. 624 (1973).

Sodium dodecyl sulfate (NaDodSO$_4$)-polyacrylamide gel electrophoresis was performed according to Swank et al, Anal. Biochem., Vol. 39, p. 467 (1971).

Light-chain allotypes were determined by Ouchterlony analysis or by radioimmunoassay, Gottlieb et al, J. Immunol., Vol. 114, p. 51 (1975).

PREPARATION OF LIGHT CHAINS AND ACID CLEAVAGE

The homogeneous antitype III pneumococcal polysaccharide antibody 3T74 was purified by affinity chromatography as described previously, Ehrlich et al, Immunochemistry, Vol. 15, p. 937 (1978). Pooled allotype b4 IgG was isolated from nonimmune serum of New Zealand white rabbits by ion-exchange chromatography on columns of diethylaminoethylcellulose (DE-52 Whatman). Ig was eluted by using 0.01 M potassium phosphate and 0.02% sodium azide (pH 7.5).

Antibody or heterogeneous IgG was reduced and alkylated, and heavy and light chains were separated by a modification described previously (Ehrlich et al., 1978).

Light chains were subjected to acid cleavage under mild conditions as described by Poulsen et al, Proc. Natl. Acad. Sci. U.S.A., Vol. 69, p. 2495 (1972). The reaction was carried out for 96 h to maximize the yield of cleavage between the $V_L(1-109)$ and $C_L(110-214)$ regions.

PREPARATION OF PROTECTED CLEAVED LIGHT CHAINS

Acid-cleaved light chains (29 mg) were dialyzed against 7 M Gdn-HCl and 0.5 M Tris-HCl, pH 8.2 (10 mg/mL), and then reduced for 90 min with 0.02 M dithiothreitol (DTT) added as a solid at 37° C. under nitrogen. To this solution was added an equal volume (3 mL) of 7 M Gdn-HCl, 0.5 M Tris-HCl, and .05 M p-chloromercuribenzoate (PCMB), pH 8.2. The mixture was incubated for 1 h at 20° C. The PCMB-treated cleaved light chains were then dialyzed against 5 M Gdn-HCl and 0.1 M sodium acetate, pH 5.5 (GAB buffer), for 16 h. As acid cleavage of the light chain for 96 h is usually 70-90% complete, cleaved and uncleaved light chains were separated by gel filtration on Sephadex G-75 equilibrated in GAB buffer. (In order to conserve material, we did not perform this step with the homogeneous light chain from antibody 3T74).

PREPARATION OF $C_L$ PEPTIDE

Complete reduction and radioalkylation of light chains, modification of the alkylated chains with citraconic anhydride, and tryptic digestion of the citraconylated chains from nonimmune pooled b4 light chains were performed according to Cannon et al., J. Immunol., Vol. 112, p. 160 (1978). Tryptic peptides from the citraconylated, fully reduced, and radioalkylated light chains were fractionated by Sephadex G-75 gel filtration and freed from salt as previously described (Cannon et al., 1978). The largest peptide obtained (residues 62-211) was acid cleaved (Poulsen et al, 1972) for 96 h and the reaction mixture applied to a 2.5×100 cm column of Sephadex G-75 equilibrated in GAB buffer. Fractions of 2.7 mL were collected and monitored for absorbance at 280 nm, and radioactivity was monitored by counting an aliquot (10 µL) in Bray's solution. Major peaks (including the $C_L$ peptide 110-211) were pooled, freed from salt by dialysis in 3500 molecular weight cutoff tubing against 10% acetic acid, and lyophilized. The conditions used for the acid cleavage were sufficient to remove simultaneously the citraconyl groups from the peptides.

PREPARATION OF $C_L$ PEPTIDE-SEPHAROSE

The $C_L$ peptide (residues 110-211) (5 mg) was dissolved in 0.1 M NaHCO$_3$, 0.5 M NaCl, and 3.5 M Gdn-HCl, pH 8.0 and reacted for 2 h at 20° C. with 2 mL of cyanogen bromide activated Sepharose 4B.

PREPARATION OF SHEEP ANTIBODIES SPECIFIC FOR RABBIT LIGHT-CHAIN CONSTANT REGION

Light chains (32 mg) from pooled nonimmune b4 rabbit Ig were completely reduced and alkylated with iodoacetic acid as previously described (Cannon et al., 1978). Following acid cleavage for 96 h, the mixture was applied to a 20 mm×125 cm Sephadex G-75 column equilibrated in 6 M urea and 1 N acetic acid in order to separate cleaved from uncleaved chains (Poulsen et al., 1972). The fractions containing cleaved light chains ($V_L + C_L$) were pooled and freed from salt on a Sephadex G-10 column, 3.5×100 cm, equilibrated in 0.03 N $NH_4OH$. The peptide mixture was lyophilized and stored at $-20°$ C.

Cleaved, reduced and carboxymethylated light chains (20 mg) were suspended in 15 mL of 0.1 M sodium phosphate buffer, pH 7.0. To this suspension was added 75 µL of 50% glutaraldehyde dropwise. The suspension (1.25% in glutaraldehyde) was stirred for 1 h at 20° C. Glutaraldehyde cross-linking of the antigen was stopped by the addition of 4 mL of 2.5 M lysine. The reaction mixtures was dialyzed repeatedly against water in acetylated membranes, followed by lyophilization.

Seventy-kilogram Shropshire sheep were immunized intramuscularly monthly for 4 months with 5 mg of glutaraldehyde cross-linked cleaved light chains with complete Freund's adjuvant. Antisera collected weekly were tested for antibody production by the ring test using fully reduced and alkylated nonimmune b4 light chains as the antigen.

Sheep antiserum (3–6 mL) containing antibodies reacting with completely reduced and alkylated b4 light chains were applied to the $C_L$ peptide-Sepharose immunoadsorbent column described above in order to isolate a fraction specific for the reduced and alkylated constant region. After being washed with PBS, the column was eluted successively with 2 M Gdn-HCl (12 mL) and then with 5 M Gdn-HCl (8 mL).

PREPARATION OF SHEEP ANTIRABBIT $C_L$ IMMUNOADSORBENT

The fraction eluted with 5 M Gdn-HCl was diluted to a protein concentration of <0.5 mg/mL and dialyzed overnight against 0.1 M $NaHCO_3$ and 0.5 M NaCl, pH 8.0, at 4° C. Precipitate was removed by centrifugation. The soluble antibodies (16 mg) were then reacted with 5 mL of CNBr-activated Sepharose 4B to make the specific anti-$C_L$ (110–211) immunoadsorbent.

PURIFICATION OF $V_L$

Acid-cleaved PCMB-treated light chians were diluted with GAB buffer until the protein concentration was less than 0.1 mg/mL. This was followed by dialysis against 6 L of PBS at 4° C. for 16 h. Preliminary dilution of the chains was necessary prior to dialysis since the PCMB-treated cleaved light chains were poorly soluble in PBS. Following dialysis, the small amount of precipitate which did appear was removed by centrifugation.

The acid-cleaved PCMB light chains (1–1.5 mg, 0.08 mg/mL) were applied to the sheep antirabbit $C_L$ peptide immunoadsorbent (4 mL) at 4° C. which had been equilibrated in PBS. The column was eluted first with PBS until no further absorbance at 280 nm could be detected. The column was then washed with GAB buffer (20 mL) to remove bound protein. Thereafter, the column was reequilibrated with PBS (10 mL). The protein fraction which had been eluted with Gdn-HCl was dialyzed extensively against distilled water and lyophilized prior to amino acid analysis and automated Edman degradation, as was an aliquot of the unbound fraction. The remainder of the unbound fraction ($V_L$) was used for activity measurements.

REOXIDATION OF $V_L$

The unbound fraction of cleaved PCMB light chains from the sheep antirabbit $C_L$ immunoadsorbent was dialyzed against 7 M Gdn-HCl and 0.5 M Tris-HCl, pH 8.2, for 16 h. The protein was reduced with 0.20 M DTT for 90 min at 37° C. under nitrogen. Thereafter, a solution containing 7 M Gdn-HCl, 0.5 M Tris-HCl, and 0.1 M mercaptoethanol was added to lower the protein concentration to less than 30 µg/mL, if necessary. The peptides were then dialyzed against 0.1 M Tris-HCl and 0.1 M mercaptoethanol, pH 8.0, at 20° C. without stirring for 6.5 h. The dialysis bag was transferred to a large volume (6) of 0.1 M Tris-acetate and 2 mM mercaptoethanol at 5° C. (pH 7.8 measured at room temperature) and dialyzed with stirring for 48 h with one change of dialysate. Since the isolated $V_L$ domain contains three cysteine residues, alkylation of the cysteine remaining after re-formation of the intradomain disulfide bridge was performed. The peptide was removed from the dialysis bag and incubated with 2.4 mM iodoacetamide for 20 min at 0° C. After dialysis overnight against 0.01 M sodium acetate, pH 5.5, at 5° C., the peptide was concentrated with Aquacide (Calbiochem) to 8 µg/mL and again dialyzed against 0.01 M sodium acetate and 0.02% sodium azide, pH 5.5, and stored at $-20°$ C.

ASSAY OF RECOMBINED ANTIBODY FRAGMENTS FOR BINDING ACTIVITY

The radiobinding assay for type III pneumococcal polysaccharide (S3) antibodies was analogous to the assay described by Chen et al., J. Immunol., Vol. 17, p. 807 (1976) and has been detailed previously (Ehrlich et al, 1978). The activity of 3T74 light chains or putative 3T74 $V_L$ was assayed by adding increasing amounts in 0.01 M sodium acetate, pH 5.5, and 0.02% sodium azide to a constant amount of 3T74 heavy chain in the same buffer. The recombined antibody or antibody fragments were added to $^{125}I$-S3-soybean trypsin inhibitor (Ehrlich et al., 1978). The antigen-antibody complex was precipitated in the presence of carrier nonimmune rabbit IgG by goat antirabbit IgG antiserum. The maximum percent binding of the $^{125}I$-S3-soybean trypsin inhibitor was 50–65% depending on the antigen preparation.

RESULTS

ISOLATION OF $C_L$ PEPTIDE (110–211) FROM NONIMMUNE RABBIT LIGHT CHAINS

Forty milligrams of fully reduced and alkylated, pooled nonimmune b4 light chains was citraconylated and subjected to tryptic digestion. The digest was fractionated by Sephadex G-75 gel filtration. The profile obtained was similar to that previously reported (Cannon et al., 1978). As the rabbit κ b4 light chain contains only one invariant arginine residue in the C region at position 211 and one invariant arginine at position 61 in the variable region, a large fragment including residues 62–211 may be isolated from this digest.

Figure 1:
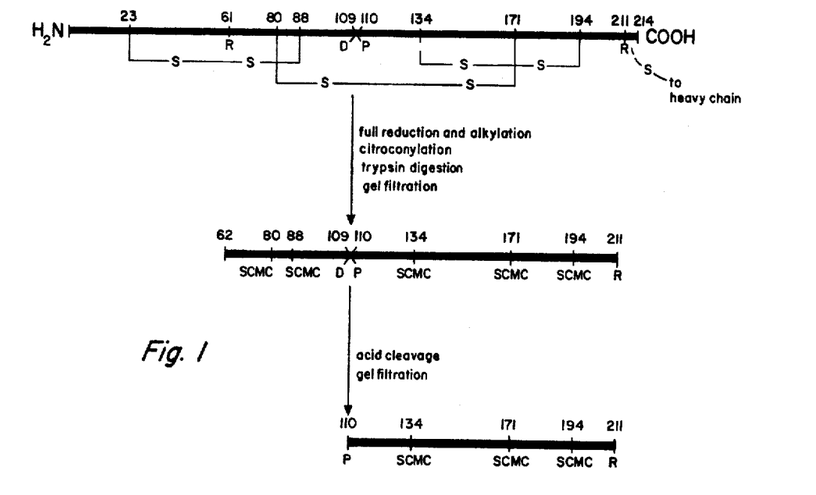
Figure 2:
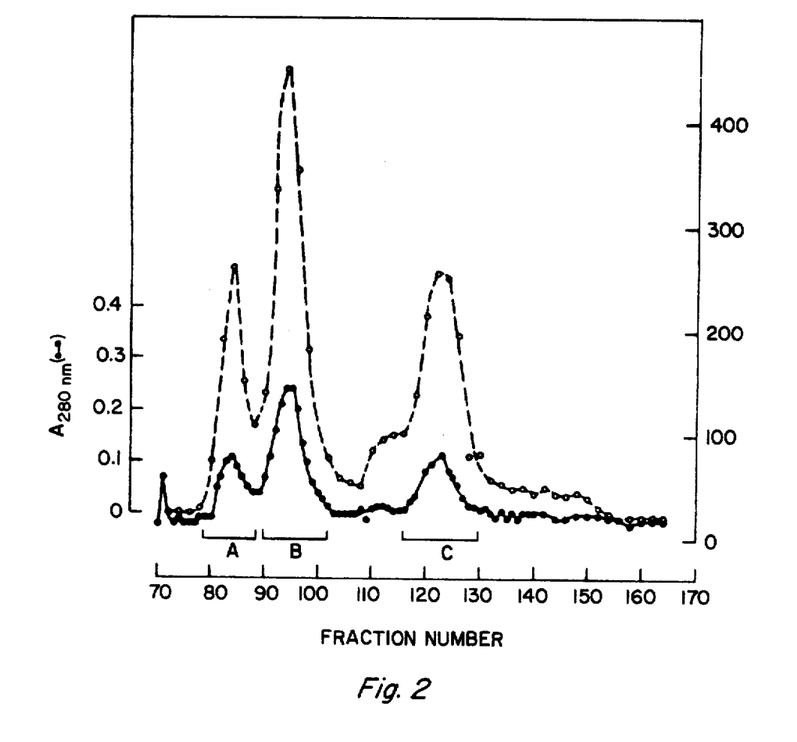

The structure of rabbit antibody b4 κ light chains is shown in FIG. 1 demonstrating the $V_L$ intradomain disulfide bridge (23-88), the $C_L$ intradomain disulfide bridge (134-194), and the interdomain disulfide bridge (80-171). The light chain may be cleaved under mild acidic conditions between aspartic acid at position 109 and proline at position 110. Invariant arginines are located at position 61 in the $V_L$ and at position 211 in the $C_L$. Following full reduction and alkylation, the citraconylated chains were digested with trypsin. The largest arginine peptide obtained spans residues 62-211. This peptide may be further cleaved in the switch region under mild acidic conditions to yield a peptide (110-211) including most of the constant region. Additional arginine residues located amino-terminal to position 61 in heterogeneous nonimmune light chains resulted in smaller fragments that did not interfere with purification of the 62-211 peptide, which was obtained in 64% yield. In order to be certain that the peptide including residues 62-211 had not undergone internal tryptic digestion on account of premature removal of citraconyl groups (Cannon et al., 1978), manual Edman degradation was carried out for three cycles on 31 nmol of peptide. A single sequence, Phe-Thr-Gly, was obtained. The yield of Pth-phenylalanine in the first cycle was 28 nmol. This sequence is identical with that beginning at position 62 in pooled b4 light chains and light chains from homogeneous antibodies. The remainder of the sample (30 mg) was subjected to mild acidic conditions known to cleave between residue 109, aspartic acid, and 110, proline (see FIGS. 1 and 2). The results of isolated of $C_L$ peptide (110-211) from nonimmune pooled b4 light chains are shown in FIG. 2. Light chains were fully reduced, alkylated, citraconylated, and digested with trypsin. The peptide spanning residues 62-211 was purified by gel filtration on Sephadex G-75 and cleaved in acid (see FIG. 1). The acid-cleaved 62-211 peptide was then applied to a 2.5 × 100 cm column of Sephadex G-75 equilibrated in GAB buffer. Fractions contained in peak B were pooled and contained the $C_L$ peptide (100-211).

The cleaved peptide was applied to a Sephadex G-75 column. The results of gel filtration are shown in FIG. 2 and are consistent with cleavage of the 62-211 peptide between residues 109 and 110. The major peak (B) was freed from salt and lyophilized. Amino acid analysis on an aliquot of this peptid is shown in Table I, where it is compared to the composition of the 110-211 peptide based on the known sequence. An aliquot (150 nmol) of the peptide from pool B was subjected to automated Edman degradation, revealing the following sequence: Pro-Val-Ala-Pro-Thr-Val-Leu-Ile-Phe-Pro. The yield of pth-valine at cycle 2 was 110 nmol. The only evidence for contaminating sequences was that for the 62-211 peptide (Phe-Thr-Gly . . . ), which was revealed by 6.5 nmol of Pth-phenylalanine at cycle 1. Thus, the 110-211 $C_L$ peptide was contaminated with ~6% of a peptide containing a portion of the variable region. The yield of the $C_L$ peptide (100-211) following acid cleavage of the 62-211 peptide was 70%. Pools A and C (FIG. 2) correspond to the uncleaved 62-211 peptide and a peptide comprising residues 62-109, respectively, and were not examined further.

TABLE I

| AMINO ACID ANALYSIS OF $C_L$ PEPTIDE 110-211 | | |
|---|---|---|
| Residues | Expected[a] | Found[b] |
| Cys[c] | 3 | 3.1 |
| Asp | 11 | 10.5 |
| Thr | 19 | 17.2 |
| Ser | 8 | 7.9 |
| Glu | 9 | 9.5 |
| Pro | 6 | 5.8 |
| Gly | 4 | 5.6 |
| Ala | 6 | 6.4 |
| Val | 12 | 11.6 |
| Ile | 3 | 2.9 |
| Leu | 4 | 4.1 |
| Tyr | 4 | 4.1 |
| Phe | 3 | 3.2 |
| His | 1 | 1.1 |
| Lys | 4 | 4.2 |
| Arg | 1 | 0.9 |
| Total | 98 | 98.1 |

[a]Composition of b4 constant region from known sequence
[b]Average of four 24-h hydrolyses. Values are not corrected for hydrolytic losses.
[c]Determined as S—(carboxymethyl)cysteine.

PREPARATION OF SHEEP ANTIRABBIT $C_L$ IMMUNOADSORBENT

The purified $C_L$ peptide (110-211) (5 mg) was coupled to CNBr-activated Sepharose. Sheep anticleaved b4 light chain antiserum (3-6 mL) was applied to this $C_L$ peptide immunoadsorbent. Sheep antibodies specific for the $C_L$ peptide (110-211) were eluted from the column with 5 M Gdn-HCl after a preliminary 2 M Gdn-HCl wash. The eluted antibodies (16 mg from three separate preparations) were dialyzed against 0.1 M sodium bicarboate and 0.5 M sodium chloride, pH 8.0, at 4° C. and coupled to 5 mL of CNBr-activated Sepharose to make the sheep antirabbit $C_L$ immunoadsorbent. The latter immunoadsorbent was used to purify $V_L$ from PCMB-protected cleaved light chains.

ISOLATION AND CHARACTERIZATION OF $V_L$ FROM NONIMMUNE POOLED LIGHT CHAINS

Nonimmune b4 pooled light chains (29 mg) were acid cleaved and fully reduced, and the cysteine residues were protected with PCMB. Uncleaved light chains were separated from the cleaved light chains by gel filtration on Sephadex G-75. NaDodSO$_4$-polyacrylamide gel analysis of the isolated cleaved light chains demonstrates that all the peptides in that fraction have a molecular weight of ~12000, corresponding to the expected size for an isolated $V_L$ and/or $C_L$ domain.

An aliquot of the cleaved light chains was subjected to sequence analysis. The sequence was compared to that of the same preparation of light chains prior to modification by acid cleavage (Table II). The amino acid sequence heterogeneity of pooled nonimmune rabbit light chains has been previously characterized and includes not only multiple amino acid subsitutions but three different amino-terminal chain lengths. Following acid cleavage, the amino acid sequence found resembles that of unmodified light chains except for an additional residue identified at cycles 1, 3, 4, 6 and 7, consistent with the known b4 constant region amino acid sequence beginning at position 110 (Pro-Val-Ala-Pro-Thr-Val-Leu . . . ). (The amino acid substitutions at cycles 2 and 5, valine and threonine, respectively, are shared by both $V_L$ and $C_L$ sequences). The sum of Pth amino acids ascribable to the $V_L$ at each position is approximately equal to the amount of Pth amino acids arising from the $C_L$ and is consistent with acid cleavage resulting in an equimolar mixture of $V_L$ and $C_L$.

Figure 3:
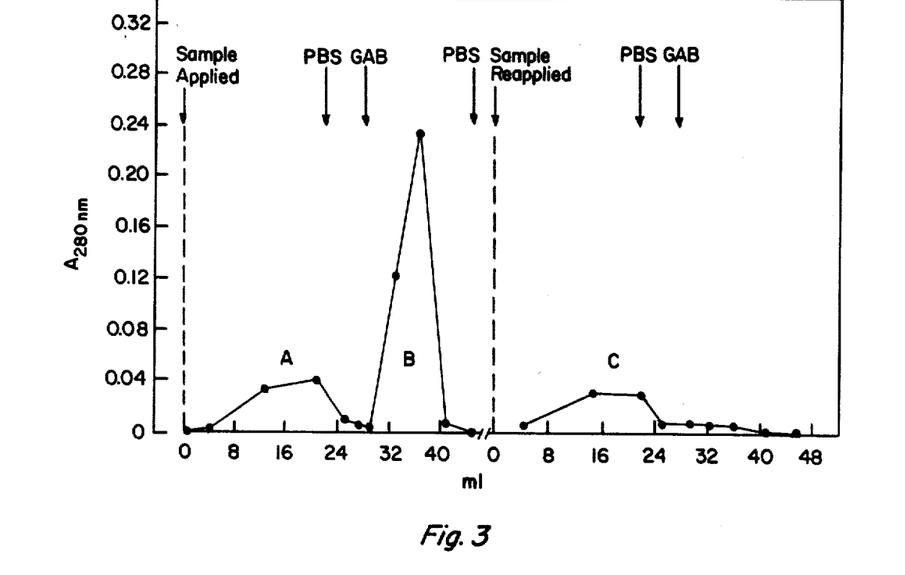

Following separation from the uncleaved light chains, the PCMB acid-cleaved light chains (1–1.5 mg) were applied to the sheep antirabbit $C_L$ immunoadsorbent. The elution profile is shown in FIG. 3. FIG. 3 shows the isolation of $V_L$ by affinity chromatography on the sheep antirabbit $C_L$ peptide column. Acid-cleaved, fully reduced, and PCMB-treated heterogeneous b4 light chains were separated from uncleaved light chains by gel filtration on Sephadex G-75 and applied in PBS to a 4-mL column of sheep antirabbit $C_L$ antibodies coupled to Sepharose 4B. The column was then washed with PBS, and the bound fraction (B) was eluted with GAB. The unbound fraction (A) was reapplied to the immunoadsorbent, and the washes were repeated. Fraction C contained pure $V_L$, while fraction B contained a mixture of $V_L$ and $C_L$ (see Table II).

As preliminary experiments demonstrated that a significant amount of residual $C_L$ (15%) remained unbound, the fallthrough fraction was reapplied to the column a second time. The results of sequence analysis of the fraction of acid-cleaved light chain that did not bind to the immunoadsorbent after a second passage are shown in Table II. The pattern of Pth amino acids obtained at each cycle resembles that of the unmodified, uncleaved light chains. Pth amino acids arising from the constant region were not identified in this fraction. In this experiment, the lower limit of detection for the stable aliphatic Pth amino acids was 0.1 nmol.

However, sequence analysis of the fraction which bound to the immunoadsorbent (Table II) indicated that, in addition to the constant region sequence, Pth amino acids arising from $V_L$ were also present. Thus, the unbound fraction consisted of pure $V_L$ while the bound fraction contained a mixture of $V_L$ and $C_L$.

ble, the method was then applied to the antibody 3T74. In this experiment a preliminary separation of cleaved and uncleaved light chains by gel filtration was not done. Thus, it was expected that the fraction bound to the immunoadsorbent would contain not only $C_L$ but also uncleaved light chains since the immunoadsorbent is expected to be specific for the sequence between residues 110 and 211. In FIG. 3B bound fractions are shown. In the unbound fraction obtained by NaDodSO₄-polyacrylamide gel patterns, there was a major band at ~12000 daltons. A band corresponding to a molecular size of uncleaved light chain was not found in this fraction, suggesting that all the uncleaved light chain remained bound to the immunoadsorbent. The gel pattern of the fraction remaining bound to the column showed, indeed, major bands at molecular weights corresponding to 12000 for the $V_L$ and/or $C_L$ and to 25000 for the intact uncleaved light chain. In both gels from bound and unbound fractions, a minor band was found with a molecular weight of 18000. This suggests that there was a minor degree of acid cleavage at a position other than that in the switch region between residues 109 and 110.

In Table III, the results of amino acid sequence analysis of both the bound and unbound fractions from the immunoadsorbent using cleaved 3T74 light chain are summarized. The amino acid sequence of the unbound fraction was identical with the known 3T74 amino-terminal light-chain sequence. On the basis of the amounts of Pth-alanine, -valine, and -leucine detected at cycles 3, 6 and 7, respectively, the unbound fraction contained 90% $V_L$. The amino acid sequence of the bound fraction on the other hand contains a mixture of $V_L$ and $C_L$. This was not unexpected, as in this experiment, in contrast to that using nonimmune pooled light chains, the cleaved and uncleaved light chains were not separated prior to affinity chromatography. Uncleaved light

TABLE II

| Sequenator Analyses of Pooled Nonimmune b4 Light-Chain Fractions | | | | | | | |
|---|---|---|---|---|---|---|---|
| | Pth Amino Acids Recovered at Each Cycle[a] | | | | | | |
| | 1 | 2 | 3 | 4 | 5 | 6 | 7 |
| Unmodified light chains | Ala(15.8) | Val(13.9) | Val(14.3) | Met(10.6) | Gln(7.6) | Gln(7.4) | Thr(5.4) |
| | Asp(3.7) | Tyr(8.7) | Leu(5.6) | Val(6.7) | Met(5.4) | Thr(3.7) | Gln |
| | Val(3.3) | Asp(4.1) | Met(1.3) | Thr(2.2) | Thr(4.7) | | |
| | Leu(1.9) | | | | | | |
| Acid-cleaved[b] light chains | Ala(11.6) | Val(23.0) | Val(7.6) | Met(5.7) | Thr(6.0) | Gln(6.7) | Thr(1.1) |
| | Asp(9.7) | Tyr(4.6) | Leu(3.4) | Val(3.3) | Gln(3.0) | Thr(1.6) | Gln |
| | Val(1.9) | Asp(7.0) | Thr(4.1) | Met(1.7) | | | |
| | Leu(1.1) | | | Gly(1.3) | | | |
| | Pro(2.9) | | Ala(14.1) | Pro(8.1) | | Val(14.8) | Leu(14.4) |
| Fraction of acid-cleaved light chains not bound to anti-$C_L$ peptide immunoadsorbent | Ala(6.4) | Val(3.4) | Val(1.9) | Met(3.6) | Met(2.4) | Thr(2.6) | Thr(2.5) |
| | Asp(1.1) | Trp(3.6) | Leu(1.5) | Val(1.7) | Gln(1.0) | | |
| | Val(1.1) | Asp(1.2) | | Thr(1.0) | Thr(1.0) | | |
| Fraction of acid-cleaved light chains binding to immunoadsorbent | Ala(7.2) | Val(21.7) | Val(4.6) | Met(2.8) | Thr(6.9) | Gln(1.7) | |
| | Asp(1.7) | Asp(21.7) | Leu(2.5) | Val(2.0) | Met(1.1) | | |
| | Val(1.6) | | Met(1.7) | Thr(1.1) | | | |
| | Pro(3.6) | | Ala(12.9) | Pro(3.2) | | Val(10.5) | Leu(10.8) |
| Expected $C_L$ sequence[c] | Pro | Val | Ala | Pro | Thr | Val | Leu |

[a]Yields (nmol) of Pth amino acids based on gas-liquid chromatography and LC are given in parentheses. Amounts less than 1 nmol are ommited, except for the unbound fraction.
[b]Following cleavage at the aspartyl-109-prolyl-110 peptide bond under mild acid conditions, light chains were fully reduced and cysteine residues were reacted with p-chloromercuribenzoate. Cleaved light chains ($V_L$ + $C_L$) were separated from uncleaved light chains by gel filtration on Sephadex G-75; an aliquot of the cleaved light chains was subjected to Edman degradation.
[c]Sequence of the rabbit κ allotype b4 light chains beginning at position 110 was reported previously.

ISOLATION AND CHARACTERIZATION OF $V_L$ FROM THE HOMOGENEOUS ANTIBODY 3T74.

As the purification of $V_L$ by affinity chromatography from pooled nonimmune light chains was proven feasible, chains as well as $C_L$ thus bind to the immunoadsorbent.

TABLE III

Sequenator Analyses of Antibody 3T74 Light-Chain Fragments[a]

| | Pth Amino Acids Recovered at Each Cycle[b] | | | | | | |
|---|---|---|---|---|---|---|---|
| | 1 | 2 | 3 | 4 | 5 | 6 | 7 |
| Not bound to anti-$C_L$ peptide immunoadsorbent | Ala(9.5) | Val(7.4) | Leu(7.0) Ala(0.7) | Thr(4.5) | Gln | Thr(2.2) Val(0.3) | Pro(1.0) Leu(0.2) |
| Bound to anti-$C_L$ peptide immunoadsorbent | Pro(1.3) Ala(2.6) | Val(6.8) | Ala(3.6) Leu(2.5) | Pro(1.9) Thr | Thr(1.8) | Val(3.0) | Leu(2.6) |
| Known sequence[c] for $C_L$ (110-) | Pro | Val | Ala | Pro | Thr | Val | Leu |
| Known $V_L$ sequence of 3T74 light chain[d] | Ala | Val | Leu | Thr | Gln | Thr | Pro |

[a]Following cleavage at the aspartyl-109-prolyl-110 peptide bond under mild acid conditions, 3T74 light chain was fully reduced and cysteine residues were reacted with p-chloromercuribenzoate. The mixture was applied to a Sepharose immunoadsorbent containing sheep antibodies rendered specific for a rabbit κ light-chain constant-region peptide (residues 110-211).
[b]Yields (nmol) of Pth amino acids as determined by gas-liquid chromatography are given in parentheses.
[c]N-terminal amino acid sequence of the rabbit κ b4 allotype light chain beginning at position 110 was previously reported.
[d]Amino-terminal sequence of the antitype III pneumococcal antibody 3T74 light chain has been previously reported.

RECOMBINATION OF $V_L$ AND HEAVY CHAIN TO PRODUCE AN ACIVE ANTIBODY FRAGMENT

The PCMB-protected $V_L$ from antibody 3T74 which had been isolated by using the sheep antirabbit $C_L$ peptide immunoadsorbent was treated with dithiothreitol and the intradomain disulfide bridge re-formed. The reoxidized $V_L$ was then recombined with heavy chain and assayed for binding capacity to type III pneumococcal polysaccharide.

Figure 4:
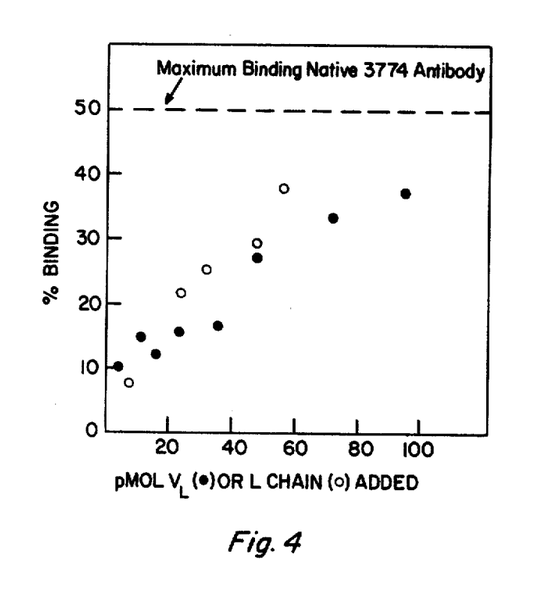

FIG. 4 shows double-antibody radioimmunoassay for binding to type III pneumococcal polysaccharide. Increasing amounts of $V_L$ or whole light chains of the homogeneous antibody 3T74 were recombined with 32 pmol of 3T74 heavy chain in 0.01 M sodium acetate and 0.02% $NaN_3$, pH 5.5, for 30 min. at 20° C. The recombinants were incubated with [$^{125}$I]-S3-soybean trypsin inhibitor for 20 min at 20° C. Following addition of 50 μg of normal rabbit Ig, goat antirabbit Ig was added and the precipitate and supernatant were counted. In this assay, the maximum binding for native 3T74 antibody was 50%. Intact heavy chain (32 pmol) or $V_L$ (95 pmol) alone bound less than 10%.

In FIG. 4, a comparison of the antigen-binding activity of the $V_L$-heavy-chain recombinant and the recombinant between heavy chain and unmodified 3T74 light chain is shown. The 3T74 $V_L$ and light chain increase the antigen binding by the same amount. In this experiment, the degree of binding due to the $V_L$ peptide alone or the heavy chain alone was <10%. The recovery of $V_L$ in the course of reoxidation and reconstitution was 29%.

The results demonstrate that, first, immunoglobulin domains differ enough from one another to be separated even in a denatured state by affinity chromatography using antibodies directed against one of the domains. This differs from prior methods which depended on selective enzymatic degradation of domains that were not desired. Second, it is of particular interest that the antigen-binding capacity of the $V_L$ domain when recombined with heavy chain is equivalent to that of intact light chain. Third, an immunoglobulin domain appears to have all the necessary information within its primary sequence to refold to the correct tertiary structure from the completely denatured state.

EXAMPLE II

This example illustrates that heavy variable chain of rabbit IgG antibody can be produced by selective enzyme cleavage and that the heavy variable chain so-obtained can be recombined with the light chain or rabbit IgG antibody to reestablish the initial antibody activity.

Protein concentrations were determined by amino acid analysis following 24 h hydrolysis at 110° in constant HCl in sealed evacuated tubes. Analyses were performed on a Durrum D-500 amino acid analyzer.

Iodination of proteins was performed according to Marchalonis, Biochem. J., Vol. 113, p. 299 (1969).

Automated Edman degradation was performed in a Beckman 890C sequencer using a 0.1 M Quadrol program described previously (Brauer et al., Biochemistry, Vol. 14, p. 3029 (1975). Phenylthiohydantoin (PTH) amino acids were identified and quantified by gas-liquid chromatography and high pressure liquid chromatography (Margolies et al, J. Chromatog., Vol. 148, p. 429 (1978). Thin-layer chromatography on polyamide sheets was also used. Criteria for PTH-amino acid identification and quantitation have been reported by Steiner et al, Biochemistry, Vol. 18, p. 4068 (1979).

Sodium dodecyl sulfate (SDS) polyacrylamide gel (12.5%) electrophoresis in 6 M urea was performed according to Swank et al., Anal. Biochem., Vol. 29, p. 462 (1971).

Digestion with pyroglutamate aminopeptidase (PCAase) was performed according to Podell et al., Biochem. Biophys. Res. Comm., Vol. 81, p. 176 (1978).

PREPARATION OF HEAVY CHAINS

The homogeneous antitype III pneumococcal polysaccharide (S3) antibody 3T74 was purified by affinity chromatography as described by Ehrlich et al., Immunochemistry, Vol. 15, p. 937 (1978). Pooled allotype al. IgG was isolated from nonimmune serum of New Zealand white rabbits by ion-exchange chromatography on columns of diethyaminoethyl cellulose (DE-52 Whatman). Ig was eluted using 0.01 M potassium phosphate, 0.02% sodium azide (pH 7.5).

Disulfide bonds of antibody of heterogeneous IgG were reduced by incubation at 37° C. for 90 min in 0.5 M Tris-HCl, 0.02 M dithiothreitol (DTT), pH 8.2 and then aminoethylated for 30 min at 20° with ethylenimine which was added in three aliquots until there was a five-fold molar excess over DTT. IgG was then dialyzed at least 4 h against 1 M acetic acid and then 18 h against 5 M guanidine-HCl, 0.1 M sodium acetate, pH 5.5. Heavy and light chains were then separated on a Sephadex G-100 column (2.5×99 cm) equilibrated in 5 M guanidine-HCl, 0.1 M sodium acetate, pH 5.5.

DIGESTION OF AMINOETHYLATED-HEAVY CHAIN AND PURIFICATION of $V_H$

Cathepsin B was purified to homogeneity from bovine liver by the process of Husain, Proteolysis and Physiological Regulation, Miami Winter Symposium, Vol. 11. p. 397. Academe Press. New York (1976) and stored at 5° in 0.02 M sodium acetate, 0.1 M sodium chloride, 0.5 mM mercuric chloride, pH 4.5.

Aminoethylated-heavy chain, after separation from light chain, was dialyzed 18 h at 5° against 0.01 M sodium acetate, pH 5.5. Cathepsin B (1.2 mg/ml) was activated by diluting the enzyme into ten volumes of 0.01 M sodium acetate pH 5.5, 0.6 mM DTT, 1.2 mM disodium ethylenediaminetetraacetic acid and heating for 5 min at 30°. Activated cathepsin was then added to the heavy chain solution (0.3-2 mg/ml) (enzymesubstrate ratio 1:150 by weight) and digestion proceeded 3.5 h. In analytical experiments aliquots of the digestion mixture were removed at various times. After SDS added 1% to each aliquot the digest samples were dialyzed against SDS polyacrylamide gel sample buffer in preparation for subsequent electrophoresis. In preparative experiments, the Cathepsin B digestion was stopped after 3.5 h by addition of 0.5 mM iodoacetic acid, and incubation at room temperature was continued for 15 min. The digestion mixture was then dialyzed for 18 h at room temperature against 5 M guanidine-HCl, 0.1 M sodium acetate, pH 5.5. Gel filtration on an Ultrogel AcA 54 column (2.4 × 90 cm) equilibrated in 3 M guanidine-HCl 0.1 M sodium acetate, pH 5.5, was then performed. Fractions containing peptides which were to be sequenced were dialyzed exhaustively against water and lyophilized.

ASSAY OF RECOMBINED ANTIBODY FRAGMENTS FOR S3 BINDING ACTIVITY

Goat anti-rabbit light chain antibody was isolated from goat anti-rabbit IgG anti-serum by affinity chromatography on a rabbit IgG light chain-Sepharose column. Light chains (7 mg) pooled heterogeneous rabbit IgG, isolated according to Ehrlich et al., 1978, supra, were reacted with 13 ml CNBr-activated Sepharose by incubation for 3 h at 20° in 0.1 M NaHCO$_3$, 0.5 M NaCl. Goat anti-rabbit IgG serum was applied to a 6.5 ml column of the light chain-Sepharose equilibrated in phosphate buffered saline (PBS). The column was washed extensively with PBS and PBS plus 3 M NaCl until the absorbance at 280 nm was less than 0.07. The anti-light chain antibodies were then eluted with 3 M NH$_4$SCN in PBS. Fractions containing eluted antibody were pooled and dialyzed against PBS for 18 h followed by dialysis against 0.1 M potassium phosphate, pH 6.5 for 4 h. The anti-light chain antibody (0.5-1.5 mg/ml) was then reacted wit hydroxysuccinimide activated Sepharose (HAS-Sepharose) (25-40 mg antibody per gram HAS-Sepharose) according to Gottleib et al., J. Immunol., Vol. 114, p. 51 (1975).

The radiobinding assay for anti-S3 antibodies was analogous to the assay described by Ehrlich et al. (1978) supra. The activity of heavy chains or putative $V_H$ from homogeneous anti-S3 antibody 3T74 was assayed by mixing the chains with a two to three-fold excess of light chains in a final concentration of 4 M guanidine HCl, 0.1 M sodium acetate, pH 5.5. The protein was then dialyzed against 0.01 M sodium acetate, 0.02% sodium azide, pH 5.5, for 18 h at 5°. The recombined antibody or antibody fragments (50 μl) were added to $^{125}$I soybean trypsin inhibitor-S3 conjugate in 0.005 M potassium phosphate, 0.15 M sodium chloride, pH 7.0 (PBS) (100 μl) and incubated at 20° C. for 20 min. A suspension of goat antirabbit light chain-Sepharose was then added (50 μl) and the mixture was kept in suspension by placing the assay tube on a rotating platform. This incubation continued for 4 h at 20° with one resuspension of the Sepharose after 2 h. The mixture was centrifuged for 1.5 min at 12,000 × g at 20° after an incubation of five min at 5°. One hundred μl of supernatant was removed and the supernatant and Sepharose including residual supernatant were counted. The percent of antigen bound was expressed as cpm in Sepharose fraction minus cpm in supernatant divided by their sum and multiplied by 100. The background was less than 5%, and the maximum binding varied from 50-65%.

DETERMINATION OF ALLOTYPE

The a1 allotypic determinants of $V_H$ were determined using a radioimmunoassay analogous to that reported by Gottleib et al (1975) supra. Samples to be assayed for allotype (0.25 to 1.25 mg/ml) were dialyzed 17 h at 4° against 0.01 M sodium acetate, 0.0% sodium azide, pH 5.5. Serial dilutions were made in 0.01 M sodium acetate, 0.02% sodium azide, 0.1 mg/ml bovine serum albumin, pH 5.5. The $V_H$, heavy chain, or IgG dilutions (125 μl) were added to $^{125}$I-IgG (allotype a1) (25 μl) in PBS containing 1 mg/ml bovine serum albumin. Anti-a1 HAS-Sepharose (50 μl) (which had been determined previously to bind 60% of the $^{125}$I-IgG) in PBS was added and the tube vigorously stirred. The Sepharose was kept in suspension by rotation for 4 h at 20°. The assay tube was then incubated for 10 min at 4° and centrifuged at 12,000 × g for 1 min. After one-half of the supernatant (100 μl) was removed the precipitate and supernatant were counted in a gamma counter for 1 min. The results are expressed as percent cpm bound which is equal to cpm in Sepharose fraction minus cpm in supernatant divided by their sum; the range of binding was 0% to 62%.

Figure 5:
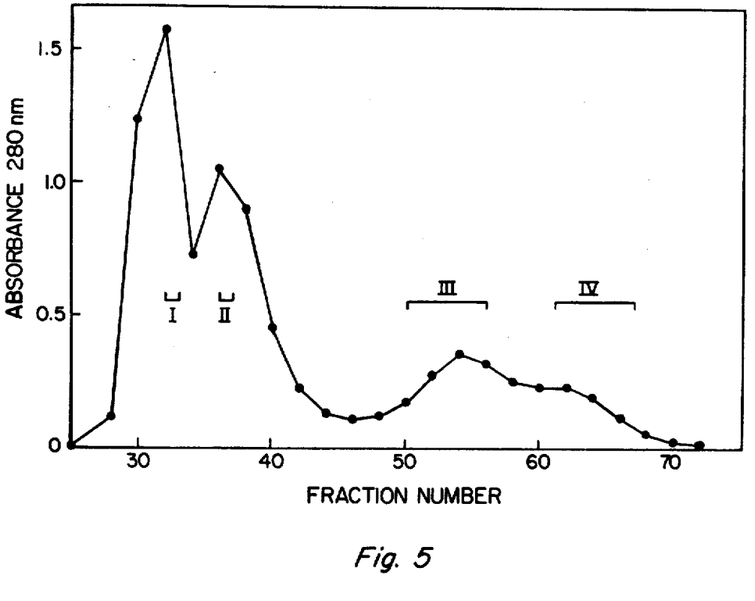

The data presented in FIGS. 5 through 8 was obtained as follows:

FIG. 5. Isolation of $V_H$ from pooled heterogeneous rabbit aminoethylated IgG heavy chain which had been digested with Cathepsin B. Aminoethylated heavy chain (73 mg) was digested with 1.46 mg Cathepsin B for 3.5 h at 20° in 0.01 M sodium acetate, pH 5.5. After stopping the reaction with iodoacetic acid, the digest was dialyzed against 3 M guanidine HCl, 0.1 M sodium acetate, pH 5.5. The protein was then chromatographed on an AcA 54 column (2.6 cm × 90 cm) equilibrated in 3 M guanidine-HCl, 0.1 M sodium acetate, pH 5.5. Fractions were 3.9 ml.

Figure 6:
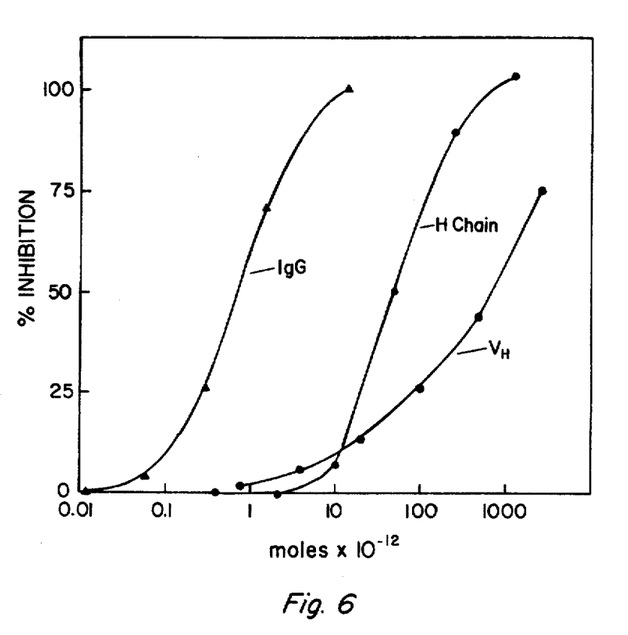

FIG. 6. Inhibition of anti-a1 allotypic antibodies. Varying amounts of IgG, heavy chain, and $V_H$ in 125 μl of 0.01 M sodium acetate, 0.02% sodium azide, pH 5.5 were added to $^{125}$I-IgG (25 μl in PBS). HAS-anti-a1 (50 μl, suspension in PBS), in an amount which could bind 60% of the $^{125}$I-IgG, was added and the assay tube rotated at 20° for 4 h. After centrifugation, 100 μl was removed and the Sepharose and supernatant fractions were counted. Binding of less than 60% indicates inhibition of the reaction between IgG and the anti-allotypic antibodies. Each point is an average of a duplicate assay.

Figure 7:
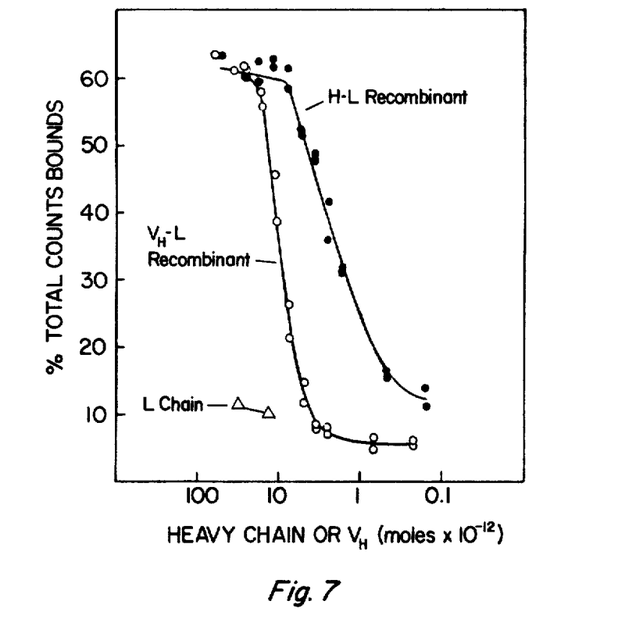

FIG. 7. Double antibody radioimmuno assay for binding to type III pneumococcal polysaccharide 3T74 $V_H$ (252 pmol) and 3T74 light chain (567 pmol) or 3T74 heavy chain (177 pmol) and 3T74 light chain (567 pmol) were dialyzed against 0.01 M sodium acetate, 0.02% sodium azide, pH 5.5 for 18 h at 5°. Serial dilutions (50 μl) were added to 100 μl $^{125}$I-S3-SBTI in PBS. After a 20 min incubation at 20°, anti-rabbit light chain HAS (50 μl in PBS) was added and the assay tubes rotated for 4 h at 20°. After centrifugation, 100 μl were removed and the Sepharose and supernatant counted. Each point is an average of a duplicate assay. Filled circles, $V_H$-light chain recombinant; open circles, heavy-light chain recombinant; triangles, light chain alone.

Figure 8:
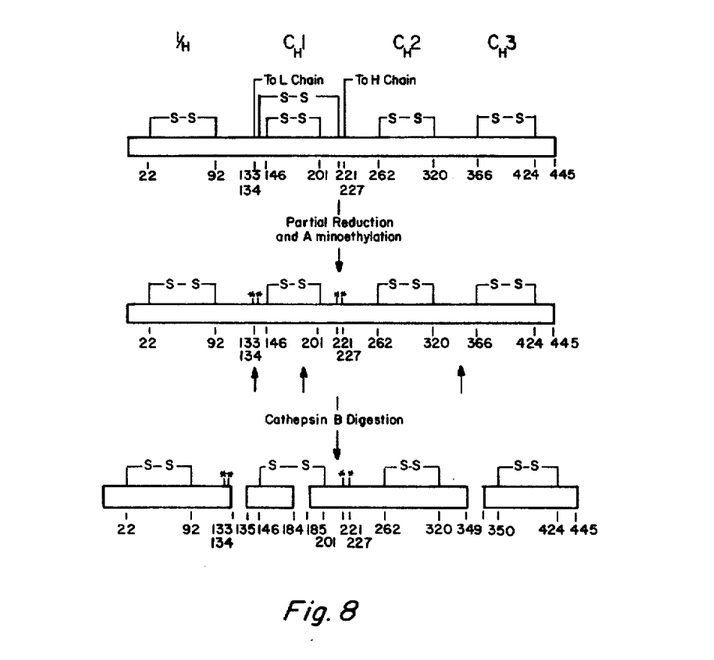

FIG. 8. Structure of partially reduced and aminoethylated rabbit heavy chain and the fragments were are produced by digestion with Cathepsin B. Numbering is by homology with the human protein DAW IgG1, Press et al., Biochem. J., Vol. 117, p. 641 (1970). Arrangement of disulfide bonds is according to O'Donnell et al., Biochem. J., Vol. 116, pp 261-268 (1970).

CATHEPSIN B DIGESTION AND ISOLATION quences were found, two of which were identical to those found in the analytical experiment. As shown in Table IV, a few minor sequences were also seen, in addition to the three major amino-terminal sequences beginning at residues 135, 184, 349. When the peptide in peak III was treated with PCAase, the amino-terminal sequence of the heavy chain starting at residue 2 was revealed. This was consistent with the removal of the amino-terminal pyroglutamic acid residue at position 1 by the action of PCAase. In the same sequence analysis, two amino acids, Valine and Leucine were found at residue 3, but this microheterogeneity is characteristic of pooled rabbit heavy chains. The peptide in peak IV also possessed the characteristic heavy chain amino-terminal sequence following treatment with PCAase. However, the major sequence in Peak IV corresponded to the heavy chain sequence which starts at residue 350.

A molecular weight range of 12,000 to 15,000 was obtained for the peptide in peak III. The peptide in peak III was assigned as $V_H$(1-136) on the basis of the molecular weight and the amino-terminal sequence as shown in Table IV. The yield of this putative $V_H$ was 13% starting from the aminoethylated-heavy chain.

| | Amino Acid Sequence of Peptide(s) Isolated from Cathepsin B Digests of Aminoethylated Pooled Rabbit IgG | | | | | | | | | | |
|---|---|---|---|---|---|---|---|---|---|---|---|
| | Yields of PTH-Amino Acid$^a$ | | | | | | | | | | Position of Assigned Sequence in |
| fraction | 1 | 2 | 3 | 4 | 5 | 6 | 7 | 8 | 9 | 10 | H Chain |
| pool I | L (11.0) | S (2.9) | S (2.5) | V (7.9) | V (7.5) | S (1.6) | V (7.7) | T (1.8) | S (4.0) | S (3.0) | 184 → |
| | G (6.4) | D (7.1) | T (2.5) | P (3.0) | S (1.9) | (S) | T (3.9) | V (5.7) | T (2.3) | L (5.6) | 135 → |
| | V (5.9) | | | | Q (1.4) | | | | A (1.0) | | unassigned |
| | | | | | | | | | P (1.3) | | |
| pool II | $^b$ | S (5.2) | S (10.4) | V (19.3) | V (15.1) | S (6.9) | V (13.2) | T (4.0) | S (5.3) | S (3.9) | 184 → |
| | | D (11.6) | T (5.6) | P (5.5) | S (4.0) | (S) | T (3.3) | V (9.0) | T (4.6) | L (7.5) | 135 → |
| | | V (7.7) | A (2.3) | E (1.4) | F (1.1) | Q (1.0) | L (6.4) | | K (5.5) | P (0.8) | unassigned |
| pool III$^c$ | S (24.5) | V (23.1) | E (19.5) | E (18.9) | S (20.2) | G (11.4) | G (12.0) | R (2.4) | L (18.6) | | 2 → |
| | | L (10.3) | | | | | | | | | |
| | L (3.8) | | | | F (3.1) | | | | | | unassigned |
| pool IV$^d$ | M (18.3) | G (7.2) | P (2.4) | P (2.4) | | E (8.5) | E (5.0) | L (8.6) | S (4.5) | S (5.0) | 350 → |
| | L (5.5) | D (4.4) | T (1.6) | V (2.7) | E (1.8) | (1.2) | L (1.5) | Y (1.0) | | | unassigned |
| | G (4.0) | | | Y (1.3) | | | T (1.1) | | | | |
| | Y (3.4) | | | | | | | | | | |

$^a$Yield in nmol of PTH-amino acids calculated from high pressure liquid chromatography and/or gas-liquid chromatography
$^b$This fraction was lost.
$^c$Pool III was sequenced after digestion with PCAase. In addition to the PTH-amino acids listed, at several positions minor PTH-amino acids less than 10% of the major sequence were detected. Pooled heterogeneous rabbit H chain, allotype a1 has two amino acid alternatives at position 4 (cycle 3).
$^d$Sequence analysis on this fraction was repeated following digestion with PCAase. An additional sequence was detected corresponding to $V_H$ beginning at residue 2.

OF $V_H$ FROM POOLED HEAVY CHAINS

In a series of analytical experiments, SDS urea gel electrophoresis indicated that a 2 to 4 digestion with Cathepsin B produced fragments which corresponded to the size of $V_H$. In addition to a small amount of heavy chain, at least five low molecular weight fragments were observed. Clearly, the Cathepsin B digestion was not restricted to the 134–135 peptide bond as anticipated. This was confirmed by a sequenator analysis of a 30 min Cathepsin B digest. Two major amino-terminal sequences were found which began at residues 135 and 184.

Thereafter, in a preparative experiment, 73 mg of aminoethylated non-immune heavy chains was digested with Cathepsin B for 3½ h. After inactivation of the enzymen with iodoacetic acid, the digest was dialyzed against 3 M guanidine-HCl, 0.1 M NaOAc, pH 5.5, and applied to a Ultrogel AcA 54 column. The results of the gel filtration experiment, shown in FIG. 5, indicated the presence of at least four peptides. When sequenator analyses of each peptide fraction (peak I-IV, 20–80 nmol) were performed, only three amino-terminal se-

INHIBITION OF AL ALLOTYPE BY $V_H$

As it is known that the a1 allotypic determinants residue on $V_H$, the putative $V_H$ was assayed for a1 allotype. As shown in FIG. 6, the protein peak III inhibits the allotypic binding of $^{125}$I(a1)IgG to anti-a1 antibodies. This inhibition was one order of magnitude less effective than intact heavy chain. The shape of the inhibition curve of $V_H$ is different from the shapes of the inhibition curves of IgG and heavy chain.

ISOLATION OF AN ACTIVE $V_H$ FROM HOMOGENEOUS RABBIT ANTIBODY 3T74

The digestion with Cathepsin B was repeated on aminoethylated heavy chain from a homogeneous anti-S3 pneumococcal polysaccharide antibody 3T74. The results of gel filtration of the digest were similar to the heterogeneous heavy chain digestion except that only one high molecular weight peak was observed. SDS urea polyacrylamide gels revealed that peak IV from the homogeneous 3T74 heavy chain digestion had a molecular weight of about 8000 while the protein in peak III had several bands in the region from 23,500 to 15,000. The contaminant in peak III with molecular weight 21,000 represented less than 10 mole percent of the total protein as determined by densitometry of the polyacrylamide gel.

The putative $V_H$ from peak III was recombined with 3T74 light chain and assayed for S3 binding. In FIG. 7, the amount of protein required to bind half the antigen is compared for the two types of recombinant molecules. The $V_H$-light chain recombinant was approximately 21% as active as the heavy chain-light chain recombinant. However, the binding curve for the $V_H$-light chain recombinant has a different shape than the binding curve for the heavy chain-light chain recombinant.

As set forth above, the $V_H$ domain from rabbit at IgG can be easily isolated from aminoethylated heavy chain following cleavage with Cathepsin B. A single digestion and gel filtration step are required. In addition, since the digestion is performed on isolated heavy chain, the likelihood of contaminating light chain or light chain fragments is small. The evidence that peak III contains predominantly $V_H$ includes: (1) SDS urea polyacrylamide gel electrophoresis reveals that the peptide in peak III was of domain size; (2) automated sequence analysis followed PCAase digestion revealed a major sequence beginning at residue 2; (3) the recombinant molecule consisting of peak III peptide and light chain (both from a homogeneous antibody) bound antigen; and (4) the peptide in peak III inhibited the binding of anti-al allotypic antibodies to al IgG.

The structure of rabbit heavy chain and the fragments produced by digestion with Cathepsin B are schematically illustrated in FIG. 8. Cathepsin B produced three major cleavages of aminoethylated heavy chain as evidenced by sequenator studies. The desired cleavages occurred between Cys$^{134}$ and Gly$^{135}$ in the sequence -Cys(AE)-Cys(AE)-Gly-Asp-, to provide $V_H$. Other cleavages occurred at the second peptide bond in the sequences which follow: Ser-Leu-Ser-Ser (residues 183–186) and Tyr-Thr-Met-Gly (residues 348–351). Although Cathepsin B recognized the sequence consisting of two adjacent aminoethyl-cysteine residues, minor sequences were found in each fraction, indicating that additional cleavages occurred. As the two adjacent aminoethylcysteine residues are located in an interdomain region, this site is especially susceptible to cleavage by Cathepsin B. In addition, the cleavage within the $C_H1$ domain (at residue 184) which occurs early in digestion, may result in a conformational change in the interdomain region between $V_H$ and $C_H1$ rendering this site more accessible to cleavage.

As the sequence analysis or PCAase digested $V_H$ peptide revealed a single major amino-terminus, the heterogeneity in the size of $V_H$ as evidenced by SDS gel electrophoresis suggests variation in length at the carboxy-terminus. This is consistent with the known dicarboxy-peptidase activity in Cathepsin B preparations. The presence of both endopeptidase activity and dicarboxypeptidase activity may be the result of the pH at which the digestion was performed (pH 5.5).

Although $V_H$ binds antigen after recombination with homologous light chain and inhibits the reaction between allotype al IgG and anti-al allotypic antibodies, it does not quantitatively replace heavy chain.

We claim:

1. The process for producing an immunogenic fragment of rabbit immunoglobulin G antibody which comprises the following steps A and/or B and C:
    A. isolating a composition rich in light variable chain by:
        a. recovering the light chain from a non-immune rabbit immunoglobulin G,
        b. reducing and alkylating said light chain,
        c. acid cleaving said light chain between aspartic acid at position 109 and proline at position 110 of said chain,
        d. purifying said acid cleaved light chain to recover a fraction rich in a fragment comprising positions 110 to 211,
        e. applying said purified fraction to a chromatographic column to effect binding of a subfraction rich in light constant chain of said rabbit immunoglobulin G,
        f. cross-linking a portion of said acid cleaved light chain,
        g. administering said cross-linked light chain into an animal species other than a rabbit,
        h. recovering anti-serum from said animal,
        i. applying said anti-serum to said column containing the light constant chain in order to attach the anti-light constant chain to said column,
        j. eluting said anti-light constant chain from said column,
        k. applying said anti-light constant chain to a second chromatographic column,
        l. acid cleaving and reducing a portion of said light chain,
        m. reacting the product of step 1 with p-chloromercuribenzoate and applying the product of step m to the column of step k and recovering a solution rich in said anti-light variable chain,
    B. isolating a composition rich in heavy variable chain by:
        a. isolating the heavy chains of non-immune rabbit immunoglobulin G,
        b. amino ethylating said heavy chain,
        c. reducing said heavy chain either concomitantly with said amino ethylation or subsequent to said amino ethylation,
        d. purifying said amino ethylated and reduced heavy chain,
        e. contacting said reduced amino ethylated heavy chain with activated cathepsin B to cleave the heavy chain at two adjacent cysteine residues at positions 133 and 134 on the peptide chain,
        f. attaching said heavy chain fragment to a chromatographic column,
        g. forming antibody to said heavy chain by injecting an animal species other than a rabbit with said heavy chain and recovering anti-sera from said animal,
        h. passing said anti-sera through said column to attach the anti-heavy constant fragment to said column,
        i. recovering an eluant rich in anti-heavy variable chain fragment;
    C. forming an immunoglobulin G fragment having substantial antibody activity by combining (1) said recovered anti-light variable chain with the complementary heavy variable chain of said rabbit immunoglobulin. (2) combining said anti-heavy variable chain fragment to the complementary light chain of said rabbit immunoglobulin G or (3)

combining said anti-light variable fragment with said anti-heavy variable fragment.

2. The process of claim 1 comprising steps A and C only.

3. The process of claim 1 comprising steps B and C only.

4. The process of claim 1 comprising steps A, B and C.

5. The process of any one of claims 1, 2, 3 or 4 wherein the chromatographic column for effecting binding of a subfraction rich in light constant chain of rabbit immunoglobulin G comprises a polysaccharide.

6. The process of claim 3 wherein said immunoglobulin G fragment is formed by combining said anti-light variable fragment with said anti-heavy variable fragment.

7. An immunologically active composition comprising anti-light variable fragment of rabbit immunoglobulin G and anti-heavy variable fragment of immunoglobulin G prepared by the process of claim 4.

8. An immunologically active composition comprising anti-light variable fragment of rabbit immunoglobulin G and the complementary heavy chain of said immunoglobulin G prepared by the process of claim 2.

9. An immunologically active composition comprising anti-heavy variable fragment of rabbit immunoglobulin G and the complementary light chain of said immunoglobulin G prepared by the process of claim 3.

* * * * *